(12) United States Patent
Doerr

(10) Patent No.: US 9,238,143 B2
(45) Date of Patent: Jan. 19, 2016

(54) IMPLANTABLE MEDICAL DEVICE WITH ELECTRODE FAULT DETECTION

(75) Inventor: Thomas Doerr, Berlin (DE)

(73) Assignee: BIOTRONIK SE & Co. KG (DE)

( * ) Notice: Subject to any disclaimer, the term of this patent is extended or adjusted under 35 U.S.C. 154(b) by 356 days.

(21) Appl. No.: 13/446,158

(22) Filed: Apr. 13, 2012

(65) Prior Publication Data

US 2012/0290028 A1 Nov. 15, 2012

Related U.S. Application Data

(60) Provisional application No. 61/484,245, filed on May 10, 2011.

(51) Int. Cl.
*A61N 1/08* (2006.01)
*A61N 1/372* (2006.01)

(52) U.S. Cl.
CPC ....... *A61N 1/37241* (2013.01); *A61N 2001/083* (2013.01)

(58) Field of Classification Search
CPC ................ A61N 1/08; A61N 1/37241; A61N 2001/083; A61N 2001/086
USPC ........................................................ 607/5–9
See application file for complete search history.

(56) References Cited

U.S. PATENT DOCUMENTS

| 5,683,430 | A | 11/1997 | Markowitz |
|---|---|---|---|
| 7,181,270 | B2 | 2/2007 | Breithardt et al. |
| 7,389,144 | B1 * | 6/2008 | Osorio et al. .................. 607/29 |
| 7,769,453 | B2 | 8/2010 | Doerr et al. |
| 7,833,191 | B2 | 11/2010 | Flach et al. |
| 7,894,476 | B2 | 2/2011 | Doerr et al. |
| 7,983,752 | B2 | 7/2011 | Doerr et al. |
| 8,014,857 | B2 | 9/2011 | Doerr |
| 8,019,415 | B2 | 9/2011 | Doerr et al. |
| 8,073,542 | B2 | 12/2011 | Doerr |
| 8,095,215 | B2 | 1/2012 | Doerr |
| 8,126,540 | B2 | 2/2012 | Doerr et al. |

(Continued)

OTHER PUBLICATIONS

Farwell et al., "Inappropriate implantable cardioverter defibrillator shocks in fractured Sprint Fidelis leads associated with 'appropriate' interrogation," *Europace* (2008) 10(6), 726-728.

(Continued)

*Primary Examiner* — Joseph Dietrich
(74) *Attorney, Agent, or Firm* — Craig A. Fieschko, Esq.; DeWitt Ross & Stevens S.C.

(57) ABSTRACT

An exemplary implantable medical device includes an electrode lead connector having at least one electrical contact for connection of an electrode lead, and an analyzing unit which is connected to the electrode lead connector and is designed to detect and evaluate a response signal present at the at least one electrical connector in response to known electromagnetic irradiation. The analyzing unit may compare a signal modulation resulting from an electromagnetic irradiation of the electrode lead with a reference signal modulation. The electrode lead may be classified as defective if the deviation exceeds a threshold deviation. If a second antenna is available, the analyzing unit may compare response signals resulting from electromagnetic irradiation of the electrode lead and the second antenna. If the ratio of response signals exceeds a threshold, the electrode lead may be classified as defective.

25 Claims, 5 Drawing Sheets

(56) References Cited

U.S. PATENT DOCUMENTS

2002/0017970 A1* 2/2002 Kinder .................. 335/299
2009/0043360 A1* 2/2009 Doerr .................... 607/59
2009/0326600 A1 12/2009 Kracker 2012/0057863 A1 5/2012 Seifert et al.

OTHER PUBLICATIONS

European Search Report, EP 12 16 4376, Mar. 17, 2014.

* cited by examiner

IMPLANTABLE MEDICAL DEVICE WITH ELECTRODE FAULT DETECTION

CROSS-REFERENCE TO RELATED APPLICATIONS

This patent application claims the benefit of U.S. Provisional Patent Application No. 61/484,245, filed on May 10, 2011, which is hereby incorporated by reference in its entirety.

FIELD OF THE INVENTION

The invention relates generally to an implantable medical device including means for detecting electrode faults. The invention relates in particular to an implantable medical device including an electrode lead connector having at least one electrical contact for connection of an electrode lead.

BACKGROUND OF THE INVENTION

Implants are known which measure electrode impedances, sensing amplitudes, pacing thresholds, or sensing signal patterns in order to check the electrode integrity. However, the known methods are not sensitive enough to detect all electrode faults as early as the initial stage, i.e. to detect electrode faults at a point in time when the therapy and diagnostic functions are not yet limited.

In Farwell et al., "Inappropriate implantable cardioverter defibrillator shocks in fractured Sprint Fidelis leads associated with 'appropriate' interrogation," *Europace* (2008) 10(6), 726-728, a case study of a defective electrode system is described, in which electromagnetic irradiation of the programmer telemetry results in inadequate shock delivery. The cited publication describes very clearly the coupling of an electromagnetic wave by a programmer device into a defective electrode system that previously showed no signs of defects. In this case the coil telemetry of the programmer device results in a typical coupling into the electrode lead which functions as an antenna. Since the defect present in the electrode lead has resulted in a permanent change to the antenna characteristic of the electrode lead in the system, this coupling is sensed as an arrhythmia signal by the electronic implant, and a shock is delivered. In contrast, if the electrode lead is intact, the irradiation of the programmer telemetry does not produce interfering signals in the input stage of the ICD.

SUMMARY OF THE INVENTION

Proceeding from this background, exemplary versions of the invention are able to detect an electrode fault at an earlier point in time and in a more specific manner than was previously possible.

An exemplary implantable medical device includes an electrode lead connector having at least one electrical contact for connection of an electrode lead. The implantable medical device further includes an analyzing unit which is connected to the electrode lead connector and is designed to detect and evaluate a response signal which is present at the at least one electrical contact in response to a known electromagnetic irradiation.

The analyzing unit is therefore capable of characterizing an electrode lead connected to the connector on the basis of the reaction of the electrode lead to an electromagnetic interference from a known source coupled to the electrode lead. The analyzing unit can be part of an implantable electronic system, which is connected or connectable to at least one electrode lead. By characterizing the electrode lead in response to an electromagnetic interference from a known source coupled into the electrode lead, the analyzing unit may also be able to determine, if applicable, that the electrode lead connector has no contact to an electrode lead due to a fault, for instance.

The exemplary implantable medical device exploits the fact that electrode leads, as antenna for coupled-in signals, have a defined antenna characteristic in the functional state and that the antenna characteristic changes in a noteworthy manner if a fault exists, thereby making it possible to detect electrode faults in electronic implants connected to electrode leads at an earlier point in time and in a more reliable manner than is possible in the related art.

The analyzing unit is preferably designed to detect and evaluate a response signal to an irradiation in the MICS frequency band. In this case the electromagnetic irradiation can originate from (for example) a programmer device which operates in the MICS band. MICS stands for "Medical Implant Communication Service" and characterizes a frequency band between 402 and 405 MHz provided for wireless communication with medical implants. Accordingly, the electromagnetic irradiation can also originate from a patient device which, as a relay station near the patient, can be used to establish a telemetric connection to an implant via the MICS band. Data exchanged between the implant and the patient device via the MICS band can be forwarded to a central service center via a wireless or wired data connection, for instance. Data or control commands from a service center can also be transmitted to the implant.

Alternatively or additionally, the analyzing unit can be designed to detect and evaluate a response signal to an irradiation output by a programmer coil of a programmer device. The electromagnetic irradiation is then the result of a programmer coil telemetry of the type carried out between a related programmer device having a programmer coil and a related coil in the implant.

In general, it is advantageous for the analyzing unit to be connected or connectable to a source of electromagnetic radiation, wherein the source of electromagnetic radiation is designed to transmit an electromagnetic wave which is suited to be coupled into an electrode lead connected to an electrode lead connector. Such a connection between analyzing unit and radiation source can be designed such that the analyzing unit can be connected wirelessly to a source of electromagnetic radiation such that the analyzing unit automatically detects the transmission of an electromagnetic wave by a particular radiation source. That is, the connection can be unilateral and passive, and can be limited to the automatic detection of electromagnetic irradiation which is suited for an electrode lead test. The connection can also include the receipt of dedicated control signals by the analyzing unit. In such cases, the analyzing unit is designed to start—in response to detection of the transmission of an electromagnetic wave by a particular radiation source—a detection and evaluation of a corresponding response signal at the at least one contact of the electrode lead connector.

It is particularly advantageous when the analyzing unit is designed to detect one of a plurality of potential radiation sources on the basis of a signal transmitted by a particular radiation source or on the basis of a particular electromagnetic wave output by a particular radiation source, and to specifically evaluate a particular response signal for a particular radiation source that was detected.

The radiation source can also be integrated into the implantable medical device. That is, the radiation source for generating an electromagnetic wave which interferes with the electrode lead can be a component of the implantable medical device itself, and the electromagnetic irradiation can be generated by the implant itself when an electrode lead test is performed.

The implantable medical device preferably includes a control unit for controlling the implantable medical device in various operating modes. The control unit can be connected to the analyzing unit and be designed to switch the implantable medical device to a corresponding, specific operating mode for the duration of the detection of a response signal by the analyzing unit. For example, the implant can be switched to a safe mode for the duration of irradiation of the electromagnetic wave.

According to a particularly preferred version of the implantable medical device, the analyzing unit is connected not only to the electrode lead connector, but also to another receiving device for an irradiated electromagnetic wave, and is designed to compare the response signal detected via the electrode lead connector with a second response signal received via the other receiving device. The analyzing unit can then compare the response to the electromagnetic irradiation at the electrode lead with a second response of the system to the irradiation, wherein the second response of the system is preferably received by an "antenna" (independent of the electrode lead) as the other receiving device. The other receiving device can be a programmer receiving coil of the implantable medical device for receiving programmer commands from an external programmer device, or it can be an antenna for MICS band telemetry.

In any case, a preferable analyzing unit is designed to evaluate a particular response signal in comparison with a reference signal which is stored or was detected in parallel, and to generate a signal indicating the presence of an electrode lead fault if the particular response signal deviates by more than a specifiable extent in regards to at least one aspect. The reference signal can be stored in a memory of the implantable medical device, or can be a reference signal that is received by the other receiving device.

BRIEF DESCRIPTION OF THE DRAWINGS

Exemplary versions of the invention are explained in greater detail using examples and with reference to the drawings. In the drawings.

DETAILED DESCRIPTION OF PREFERRED VERSIONS OF THE INVENTION

Figure 1:
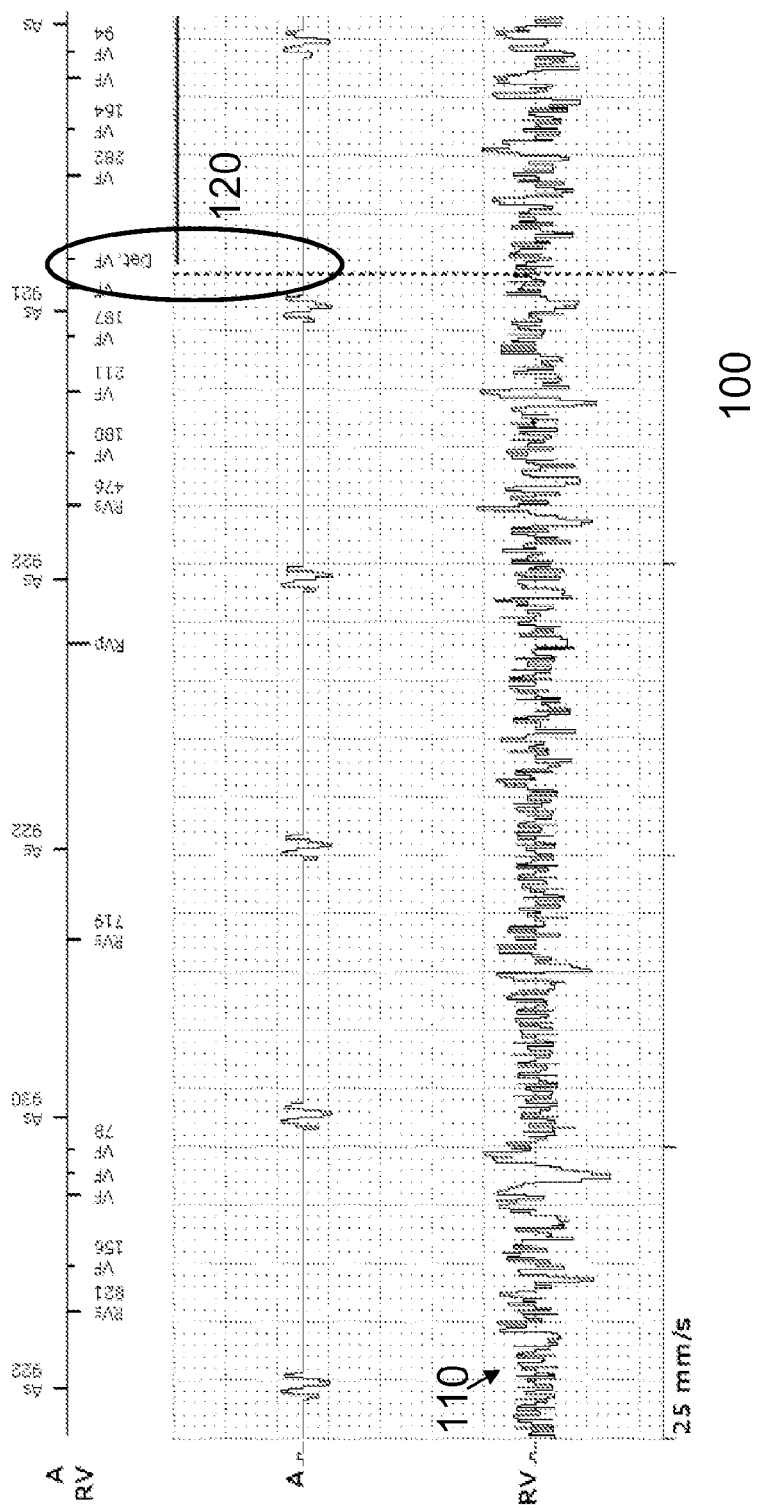
FIG. 1: shows the effect of a faulty electrode lead by way of an electrocardiogram used as an example.

FIG. 1 shows an example of an electrocardiogram 100, which depicts an interference coupled into a defective electrode lead of an implantable defibrillator (ICD) via programmer coil telemetry (i.e. a programmer device or an external patient device). The coupled-in interference is expressed in the right-ventricular intracardial electrocardiogram (IEMG) 110 recorded by a right-ventricular sensing electrode (RV), and therefore in right-ventricular IEGM channel 110. The interference results in an erroneous detection of ventricular fibrillation (see reference character 120), thereby initiating the process of charging a capacitor for providing energy for a defibrillation shock.

Figure 2:
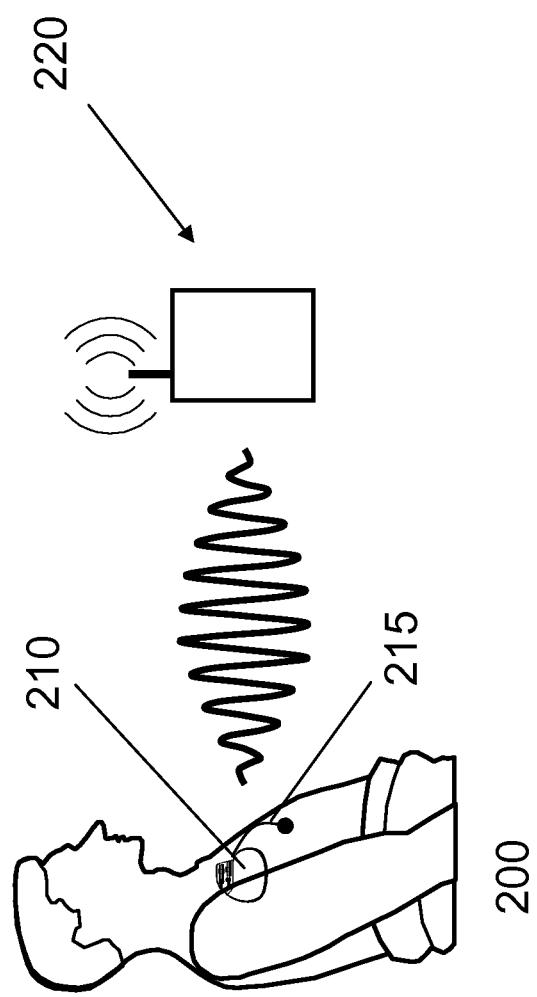
FIG. 2: shows a system including an implantable medical device and an external device as radiation source.

FIG. 2 represents a system including an implantable medical device 210—which is also referred to below as an implant—and an external programmer device or patient device 220. The figure shows a patient 200 with an electronic implant 210 and an electrode lead 215 connected thereto. In the case of telemetric data transmission from the patient device/programmer device 220, for instance, a defined electromagnetic irradiation is coupled into electrode lead 215 by the patient device/programmer device 220 as the radiation source known by the system. Such a radiation source can be (for example) the programmer device or the patient device for home monitoring. Ideally, an electromagnetic wave with a carrier frequency that is required anyway for communication is utilized as the electromagnetic irradiation, although any other frequencies for electrode diagnostics may be irradiated.

Figure 3:
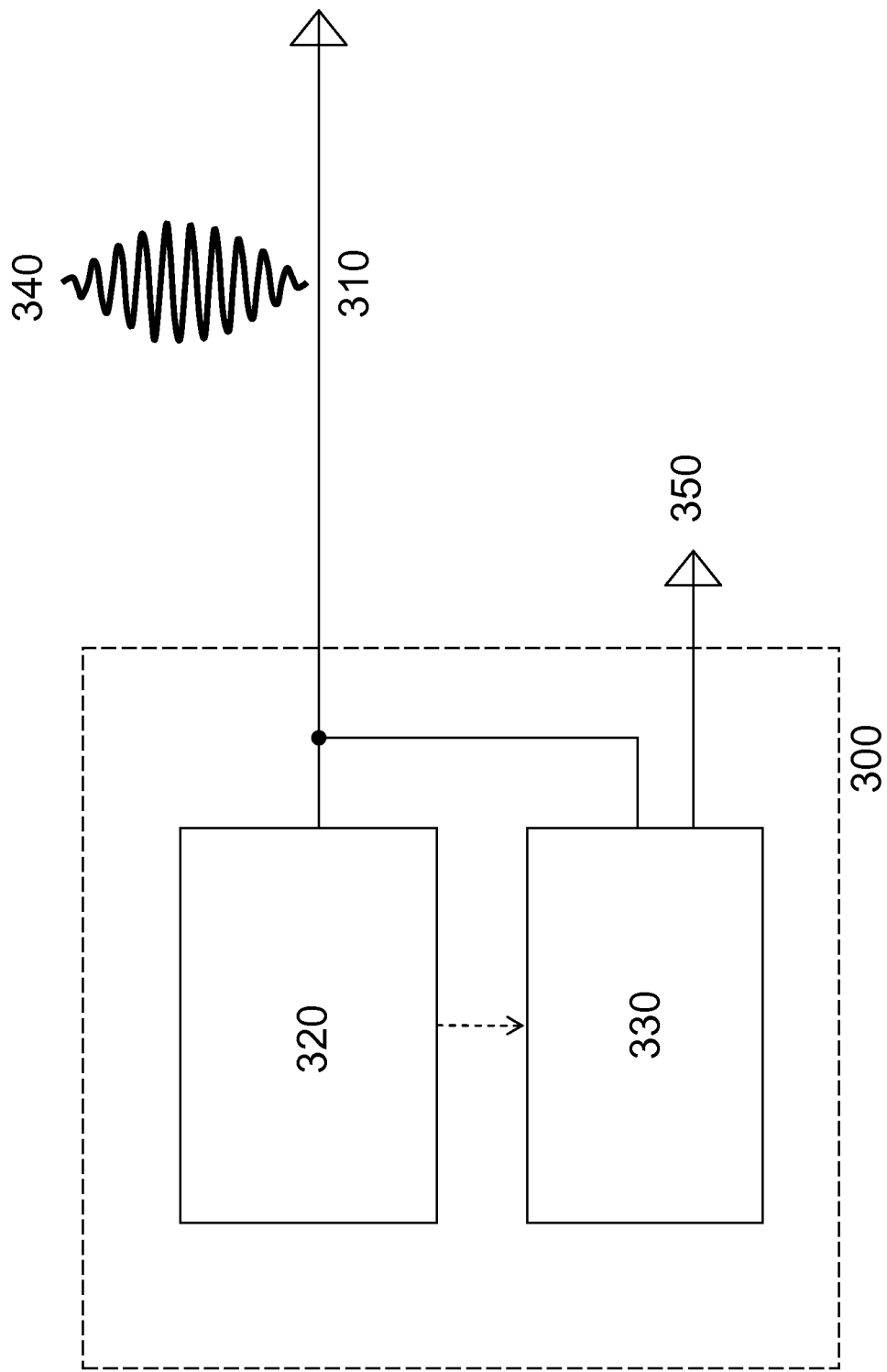
FIG. 3: shows a simplified block diagram of an implantable medical device.

FIG. 3 shows a simplified block diagram of an exemplary implant 300, in which the usual components of known implantable cardiac stimulators such as sensing units, stimulation units, control and evaluation units are omitted for simplicity. Implant 300 is connected to at least one electrode lead 310. The signals received by electrode lead 310 are supplied to control unit 320 used for therapy and diagnostics. In this version of the invention, a second analyzing unit 330, which is connected to the electrode connector, is also provided for evaluating the electromagnetic signal response at an electrode lead connector. Analyzing unit 330 may be designed to know or detect the signal modulations that occur at the electrode lead connector in the faultless state of the electrode lead as a result of known electromagnetic irradiation 340. Deviation in the expected signal modulations can therefore be detected as a potential electrode fault.

The presence of a known electromagnetic irradiation can be communicated to analyzing unit 330 via (for example) the communication connection that has been established with the programmer device. For example, the programmer device can transmit a signal which is received and processed by control unit 320 or analyzing unit 330, and which indicates that a telemetric connection has been established, or control unit 320 immediately signals to analyzing unit 330 when a telemetric connection with the programmer device has been established. This is a preferred solution which is indicated in FIG. 3 using a dashed line.

In addition, a second antenna 350 of the implant, which is independent of the electrode lead to be evaluated, can be used to receive an irradiated electromagnetic wave and to improve the evaluation of the response signal. Using the second antenna 350 it is possible for analyzing unit 330 to compare the response signal received via electrode lead 310, and the reference signal received via second antenna 350 as the reference antenna. Analyzing unit 330 is preferably designed such that it classifies electrode lead 310 as defective if the ratio of response signal to reference signal exceeds a certain value. In addition, analyzing unit 330 is preferably designed such that it triggers a signal if the reference signal is too low, i.e. lower than a specified lower limit value. This signal can trigger the output of a notice to a user instructing him to move the interference transmitter closer to the implant.

Figure 4:
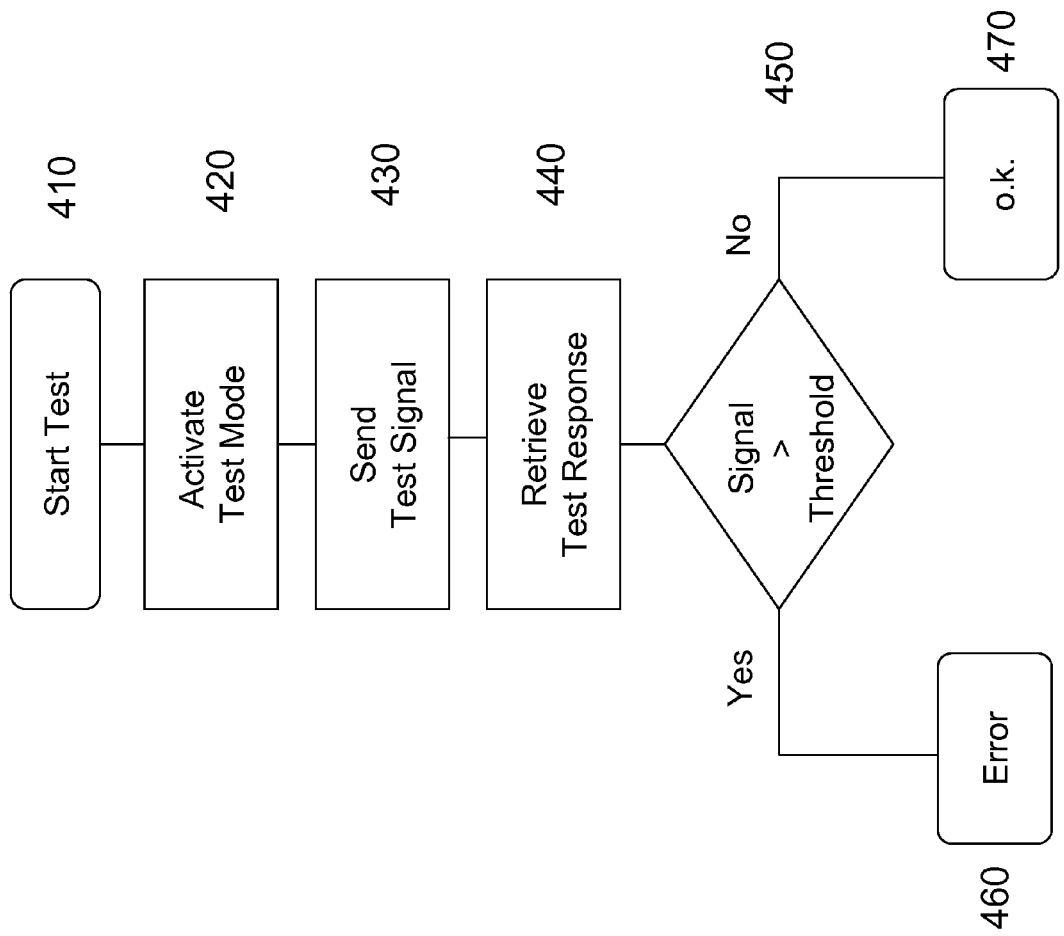
FIG. 4: shows a flow chart for illustrating a mode of operation of the implantable medical device depicted in FIG. 3.

FIG. 4 shows one possible procedure for an electrode test. The electrode test is started automatically (410) within the scope of an aftercare examination by the programmer device. First, the programmer device transmits a command for test initialization (420) to the implant, thereby deactivating the electrode lead(s), for instance, for therapy control in order to prevent unwanted interference of the course of therapy. In the case of a dual-chamber or three-chamber pacemaker including an atrial electrode lead and a ventricular electrode lead, the operating mode can be changed to VVI when testing the atrial electrode lead, for instance. In the VVI operating mode, only signals from the ventricular electrode lead are processed.

Next, the programmer device transmits (430) the electromagnetic wave, as the interference signal, via a suitable antenna to the implant which then evaluates the signals that were received. At the end of the test, the test response is retrieved (440) from the analyzing unit of the implant, and the value thereof is evaluated (450). If a deviation of the response signal from a stored or received reference signal measured at the electrode lead exceeds a limit value, the corresponding electrode lead is classified as faulty (460) or okay (470).

Figure 5:
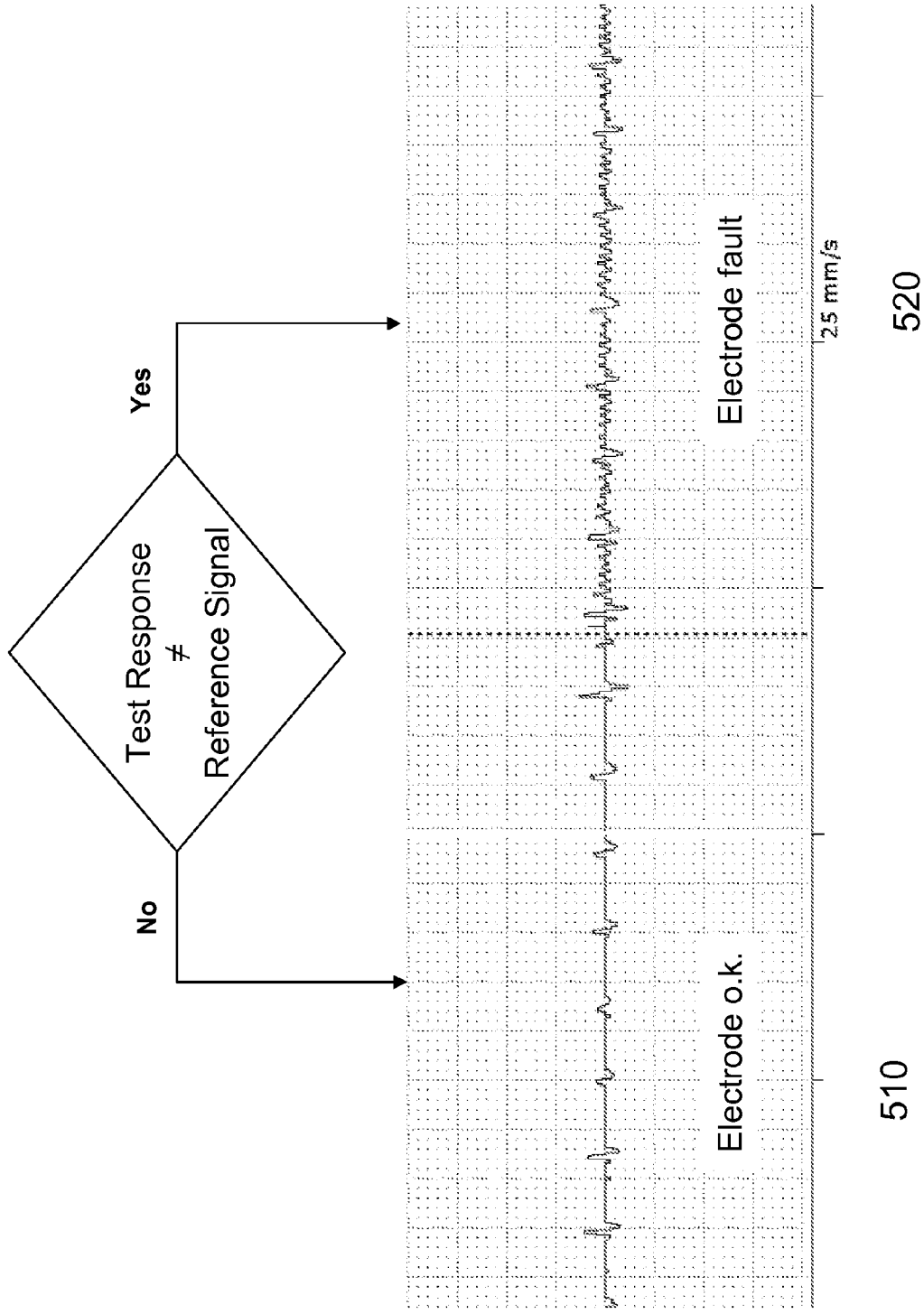
FIG. 5: shows a test signal.

FIG. 5 shows, as an example, the electrode signals that may result when the interference signal is irradiated, and which are to be analyzed by the analyzing unit in the implant. Shown in the left section of the figure is a response signal 510 associated with an intact electrode lead, and the irradiated signal is not visible on the electrode lead. Shown in the right section 520 of the figure is a response signal which occurs when the electrode lead is not intact, and therefore the irradiated signal from the radiation source is clearly visible.

The analyzing unit in the implant or the programmer device can use simple spectral analysis, for instance, to analyze these signals, in order to detect the presence of the irradiated interference.

In addition, a comparison of the response signal, which is detectable at the contact for the electrode lead, with a reference signal which can be detected at an independent antenna can be evaluated, and the ratio thereof can be compared for error analysis.

The irradiated interference signals can also contain timing/pulse sequences to simplify identification.

The solution provided by exemplary versions of the invention promises to greatly increase the sensitivity of electrode fault detection and the possibility of much earlier detection of electrode faults. The method can be used for all types of electrode leads, even for those that are not accessible to a "classical" electrode integrity test (e.g. supply leads for an implanted sensor). The evaluation of the signals can be designed to be robust using very simple means of signal processing, thereby resulting in low additional costs combined with good sensitivity and specificity.

It will be apparent to those skilled in the art that numerous modifications and variations of the described examples and versions are possible in light of the above teaching. The disclosed examples and versions are presented for purposes of illustration only. Other alternate versions may include some or all of the features disclosed herein. Therefore, it is the intent to cover all such modifications and alternate versions as may come within the true scope of this invention.

What is claimed is:

1. An implantable medical device including:
   a. an electrode lead connector having at least one electrical contact for connection of an electrode lead; and
   b. an analyzing unit connected to the electrode lead connector, the analyzing unit being configured to:
      i. detect a response signal present at the at least one electrical contact, the response signal occurring in response to known electromagnetic irradiation;
      ii. evaluate the response signal to determine whether there is an electrode lead fault; and
      iii. generate a signal indicating there is an electrode lead fault if evaluation of the response signal indicates there is an electrode lead fault.

2. The implantable medical device of claim 1 wherein the analyzing unit is configured to detect and evaluate a response signal to irradiation in the MICS frequency band.

3. The implantable medical device of claim 1:
   a. in combination with a programmer device:
      (1) having a programmer coil, and
      (2) configured to communicate programming to the medical device via the programmer coil;
   b. wherein the analyzing unit is configured to detect and evaluate a response signal to irradiation output by the programmer coil of the programmer device.

4. The implantable medical device of claim 1 wherein:
   a. the analyzing unit is connected or connectable to a source of electromagnetic radiation; and
   b. the source of electromagnetic radiation is configured to transmit an electromagnetic wave which is suited to be coupled into the electrode lead connected to the electrode lead connector.

5. The implantable medical device of claim 4 wherein:
   a. the analyzing unit is wirelessly connectable to a source of electromagnetic radiation such that the analyzing unit automatically detects the transmission of an electromagnetic wave by a particular radiation source; and
   b. the analyzing unit is configured to start, in response to the detection of the transmission of the electromagnetic wave by the particular radiation source, the detection and evaluation of a corresponding response signal at the at least one contact of the electrode lead connector.

6. The implantable medical of claim 5 wherein the analyzing unit is configured to:
   a. detect one of a plurality of potential radiation sources on the basis of:
      i. a signal transmitted by a particular radiation source, or
      ii. a particular electromagnetic wave output by a particular radiation source; and
   b. specifically evaluate a particular response signal for a particular radiation source that was detected.

7. The implantable medical device of claim 1 further including an electromagnetic radiation source integrated therein.

8. The implantable medical device of claim 1 further including a control unit configured to control the implantable medical device in various operating modes, wherein the control unit is:
   a. connected to the analyzing unit; and
   b. configured to switch the implantable medical device to a deactivated-lead operating mode wherein:
      i. a particular electrode lead to be tested is deactivated, whereby the particular electrode lead cannot receive signals that influence therapy, and
      ii. the deactivated-lead operating mode is maintained for the duration of the detection of a response signal by the analyzing unit.

9. The implantable medical device of claim 1 wherein:
   a. the electrode lead connector is a first receiving device;
   b. the implantable medical device further includes a second receiving device for an irradiated electromagnetic wave;
   c. the analyzing unit is configured to compare the response signal detected via the electrode lead connector with a second response signal received via the second receiving device.

10. The implantable medical device of claim 9 wherein the second receiving device is a programmer receiving coil of the implantable medical device, the programmer receiving coil being configured to receive programmer commands from an external programmer device.

11. The implantable medical device of claim 9 wherein the second receiving device is defined by an antenna of the implantable medical device, the antenna being configured for telemetry in the MICS frequency band for exchanging data with an external programmer device.

12. The implantable medical device of claim 1 wherein the analyzing unit is configured to:
   a. evaluate a particular response signal in comparison with a reference signal which is stored or was detected in parallel; and
   b. generate a signal indicating the presence of an electrode lead fault if the particular response signal deviates by more than a specifiable extent.

13. The implantable medical device of claim 1:
   a. further including an antenna in communication with the analyzing unit; and
   b. wherein the analyzing unit is further configured to:
      (1) detect a first response signal present at the at least one electrical contact in response to known electromagnetic irradiation;
      (2) detect a second response signal resulting from the antenna encountering the known electromagnetic irradiation; and
      (3) determine whether the electrode lead is defective in dependence on the first and second response signals.

14. The implantable medical device of claim 13 wherein the analyzing unit determines whether the electrode lead is defective by:
   a. determining a ratio of the first and second response signals; and
   b. comparing the ratio versus a threshold ratio value.

15. The implantable medical device of claim 13 wherein the known electromagnetic irradiation is in the MICS frequency band.

16. The implantable medical device of claim 13:
   a. in combination with a programmer device configured to communicate with the implantable medical device via a programmer coil provided on the medical device, and
   b. wherein the antenna is defined by the programmer coil.

17. An implantable medical device having:
   a. an electrode lead configured to be secured to a patient; and
   b. an analyzing unit configured to:
      i. receive a signal modulation in the electrode lead, the signal modulation resulting from an electromagnetic irradiation;
      ii. compare the signal modulation to a reference signal modulation to obtain a level of deviation, the reference signal modulation being representative of a faultless operation of the electrode lead; and
      iii. classify the electrode lead as defective if the level of deviation between the signal modulation and the reference signal modulation exceeds a threshold level of deviation.

18. The implantable medical device of claim 17 wherein:
   a. the electrode lead functions as a first antenna; and
   b. the antenna function of the electrode lead significantly differs between:
      i. a faultless state in which the electrode lead is functioning properly; and
      ii. a defective state in which the electrode lead is not functioning properly.

19. The implantable medical device of claim 18 wherein the analyzing unit is further configured to:
   a. receive a first response signal resulting from the electrode lead encountering an electromagnetic irradiation;
   b. receive a second response signal resulting from a second antenna encountering an electromagnetic irradiation;
   c. determine a ratio of the first response signal to the second response signal; and
   d. classify the electrode lead as defective if the ratio exceeds a threshold ratio value.

20. The implantable medical device of claim 19 wherein the second antenna is a programmer coil of a programmer device.

21. The implantable medical device of claim 17 wherein the electromagnetic irradiation originates from a programmer device.

22. The implantable medical device of claim 17 further including an internal irradiation source, wherein the electromagnetic irradiation results from the internal irradiation source.

23. A method of operating an implantable medical device, the method including the steps of:
   a. securing an electrode lead to a patient; and
   b. using an analyzing unit to:
      i. receive a signal modulation in the electrode lead, the signal modulation resulting from an electromagnetic irradiation;
      ii. compare the signal modulation to a reference signal modulation to obtain a level of deviation, the reference signal modulation representative of a faultless operation of the electrode lead; and
      iii. classify the electrode lead as defective if the level of deviation exceeds a threshold level of deviation.

24. The method of claim 23 wherein the electrode lead functions as a first antenna, the method further including the steps of using the analyzing unit to:
   a. receive a first response signal detected in the MICS frequency band, the first response signal resulting from the electrode lead encountering an electromagnetic irradiation;
   b. receive a second response signal detected in the MICS frequency band, the second response signal resulting from a second antenna encountering an electromagnetic irradiation;
   c. determine a ratio of the first response signal to the second response signal; and
   d. classify the electrode lead as defective if the level of deviation between the signal modulation and the reference signal modulation exceeds a threshold level of deviation.

25. The method of claim 23 wherein the reference signal modulation is received by a programmer coil provided on the medical device, the programmer coil being configured to receive transmissions from an external programming device.

* * * * *